US00PP26503P2

(12) United States Plant Patent
Oostveen

(10) Patent No.: US PP26,503 P2
(45) Date of Patent: Mar. 15, 2016

(54) ***ANISODONTEA* PLANT NAMED 'OOSTANIQUE'**

(50) Latin Name: *Anisodontea capensis*
Varietal Denomination: Oostanique

(71) Applicant: Cornelis A. Oostveen, De Kwakel (NL)

(72) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 240 days.

(21) Appl. No.: 13/998,608

(22) Filed: Nov. 15, 2013

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — C. A. Whealy

(57) ABSTRACT

A new and distinct cultivar of *Anisodontea* plant named 'Oostanique', characterized by its upright and outwardly spreading plant habit; freely branching habit; dense and bushy plant form; relatively large leaves; freely flowering habit; relatively large dark pink-colored flowers; and good postproduction longevity.

2 Drawing Sheets

Botanical designation: *Anisodontea capensis.*
Cultivar denomination: 'OOSTANIQUE'.

BACKGROUND OF THE INVENTION

The present invention relates to a new and distinct cultivar of *Anisodontea* plant, botanically known as *Anisodontea capensis*, and hereinafter referred to by the name 'Oostanique'.

The new *Anisodontea* plant is a product of a planned breeding program conducted by the Inventor in De Kwakel, The Netherlands. The objective of the breeding program is to create new freely-flowering *Anisodontea* plants with good postproduction longevity.

The new *Anisodontea* plant originated from a self-pollination made by the Inventor in De Kwakel, The Netherlands in July, 2010 of *Anisodontea capensis* 'Oostani', not patented. The new *Anisodontea* plant was discovered and selected by the Inventor as a single flowering plant from within the progeny of the stated self-pollination in a controlled environment in De Kwakel, The Netherlands in May, 2011.

Asexual reproduction of the new *Anisodontea* plant by terminal cuttings in a controlled environment in De Kwakel, The Netherlands since August, 2011 has shown that the unique features of this new *Anisodontea* plant are stable and reproduced true to type in successive generations.

SUMMARY OF THE INVENTION

Plants of the new *Anisodontea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oostanique'. These characteristics in combination distinguish 'Oostanique' as a new and distinct *Anisodontea* plant:

1. Upright and outwardly spreading plant habit.
2. Freely branching habit; dense and bushy plant form.
3. Relatively large leaves.
4. Freely flowering habit.

5. Relatively large dark pink-colored flowers.
6. Good postproduction longevity.

Plants of the new *Anisodontea* can be compared to plants of the female parent, 'Oosanti'. Plants of the new *Anisodontea* differ from plants of 'Oostani' in the following characteristics:

1. Plants of the new *Anisodontea* grow faster than plants of 'Oostani'.
2. Plants of the new *Anisodontea* have larger leaves than plants of 'Oostani'.
3. Flowers of plants of the new *Anisodontea* are darker pink in color than flowers of plants of 'Oostani'.

Plants of the new *Anisodontea* can be compared to plants of unnamed selections of *Anisodontea capensis* known to the Inventor. In side-by-side comparisons conducted in De Kwakel, The Netherlands, plants of the new *Anisodontea* differed from plants of the unnamed selections in the following characteristics:

1. Plants of the new *Anisodontea* had larger leaves than plants of the unnamed selections known to the Inventor.
2. Plants of the new *Anisodontea* had larger flowers than plants of the unnamed selections known to the Inventor.
3. Flowers of plants of the new *Anisodontea* were darker pink in color than flowers of plants of the unnamed selections known to the Inventor.

BRIEF DESCRIPTION OF THE PHOTOGRAPHS

The accompanying colored photographs illustrate the overall appearance of the new *Anisodontea* plant showing the colors as true as it is reasonably possible to obtain in colored reproductions of this type. Colors in the photographs may differ slightly from the color values cited in the detailed botanical description which accurately describe the colors of the new *Anisodontea* plant.

The photograph on the first sheet comprises a side perspective view of a typical flowering plant of 'Oostanique' grown in a container.

The photograph on the second sheet is a close-up view of typical flowers of 'Oostanique'.

DETAILED BOTANICAL DESCRIPTION

The aforementioned photographs and following observations, measurements and values describe plants grown during the late summer in 25-cm containers in a glass-covered greenhouse in De Kwakel, The Netherlands and under cultural practices typical of commercial *Anisodontea* production. During the production of the plants, day temperatures ranged from 15° C. to 25° C. and night temperatures ranged from 10° C. to 20° C. Plants were pinched one time and were two years old when the photographs and the description were taken. In the following description, color references are made to The Royal Horticultural Society Colour Chart, 2007 Edition, except where general terms of ordinary dictionary significance are used.

Botanical classification: *Anisodontea capensis* 'Oostanique'.

Parentage:

*Female, or seed, parent.*—*Anisodontea capensis* 'Oostani', not patented.

*Male or pollen parent.*—*Anisodontea capensis* 'Oostani', not patented.

Propagation:

*Type.*—By terminal cuttings.

*Time to initiate roots, summer.*—About ten days at temperatures about 22° C.

*Time to initiate roots, winter.*—About two weeks at temperatures about 18° C.

*Time to develop roots, summer.*—About three weeks at temperatures about 22° C.

*Time to develop roots, winter.*—About four weeks at temperatures about 18° C.

*Root description.*—Medium in thickness, fibrous; white to light brown in color.

*Rooting habit.*—Freely branching; dense.

Plant description:

*Plant form and growth habit.*—Upright and outwardly spreading plant habit; moderately vigorous to vigorous growth habit.

*Branching habit.*—Freely branching habit, usually about 60 lateral branches developing per plant; bushy and dense plant form.

*Plant height.*—About 94.5 cm.

*Plant diameter* (*area of spread*).—About 86 cm.

Lateral branch description:

*Length.*—About 36.5 cm.

*Diameter.*—About 3 mm.

*Internode length.*—About 3.7 cm.

*Texture.*—Pubescent; rugose.

*Strength.*—Moderately strong to strong.

*Color, immature.*—Between 137B and 143A.

*Color, mature.*—Close to 199A; stripes, close to N199B to N199C.

Leaf description:

*Arrangement.*—Alternate, simple.

*Length.*—About 5.5 cm.

*Width.*—About 5.4 cm.

*Shape.*—Hastate.

*Apex.*—Rounded to irregularly retuse.

*Base.*—Truncate.

*Margin.*—Irregularly crenate.

*Texture, upper and lower surfaces.*—Pubescent.

*Venation pattern.*—Palmate; reticulate.

*Color.*—Developing leaves, upper surface: Close to 137B. Developing leaves, lower surface: Close to 138A to 138B. Fully developed leaves, upper surface: Close to N137C; venation, close to 143A to 143B. Fully developed leaves, lower surface: Close to 137B; venation, close to 143A to 143B.

*Petioles.*—Length: About 2 cm. Diameter: About 1.5 mm. Texture, upper and lower surfaces: Pubescent. Color, upper and lower surfaces: Close to 143A.

Flower description:

*Flower arrangement.*—Flowers axillary, either singly or in pairs; freely flowering habit with usually about 20 flowers developing per lateral branch; flowers face upright to slightly outwardly.

*Natural flowering season.*—Plants flower continuously from spring until autumn in The Netherlands; plants begin flowering about four months after planting.

*Flower longevity.*—Flowers last about five days on the plant; flowers not persistent.

*Fragrance.*—None detected.

*Flower diameter.*—About 3.6 cm.

*Flower length* (*height*).—About 1.5 cm.

*Flower buds.*—Length: About 1.2 cm. Diameter: About 8 mm. Shape: Broadly elliptic to rhomboidal. Color: Close to 138B.

*Petals.*—Arrangement: Corolla consists of five petals in a single whorl. Length: About 1.8 cm. Width: About 2 cm. Shape: Obcordate. Apex: Emarginate. Base: Attenuate. Margin: Entire. Texture, upper and lower surfaces: Smooth, glabrous, luster, matte and at the base, glossy. Color: When opening, upper and lower surfaces: Close to 64B; towards the base, close to 61A; venation, close to 61A. Fully opened, upper and lower surfaces: Close to 64B to 64C; towards the base, close to 61A; venation, close to 61A; color becoming closer to 71A to 71B with development.

*Sepals.*—Appearance: Five sepals fused into a star-shaped calyx. Length: About 1.3 cm. Width: About 6 mm. Shape: Elliptical. Apex: Acute. Base: Broadly cuneate. Margin: Entire. Texture, upper and lower surfaces: Densely pubescent. Color: When opening, upper surface: Close to 143C. When opening, lower surface: Close to 138B. Fully opened, upper surface: Close to 143B. Fully opened, lower surface: Close to 138A.

*Peduncles.*—Length: About 1.5 cm. Diameter: About 1.5 mm. Angle: About 40° from stem axis. Strength: Moderately strong. Texture: Pubescent. Color: Close to 138A to 138B.

*Reproductive organs.*—Androecium: Stamen number: About 100. Filament length: About 2 mm. Filament color: Close to 64A. Anther shape: Orbicular. Anther length: About 0.75 mm. Anther color: Close to 203A. Amount of pollen: Moderate to abundant. Pollen color: Close to N187D. Gynoecium: Pistil length: About 1 cm. Style length: About 9 mm. Style color: Close to 60B. Stigma appearance: Club-shaped. Stigma color: Close to 54B. Ovary color: Close to 150C to 150D.

*Seeds and fruits.*—Seed and fruit development has not been observed on plants of the new *Anisodontea*.

Garden performance: Plants of the new *Anisodontea* have been observed to have good garden performance and to tolerate rain, wind, high temperatures about 40° C. and to be hardy to USDA Hardiness Zone 8.

Pathogen & pest resistance: Plants of the new *Anisodontea* have not been shown to be resistant to pathogens and pests common to *Anisodontea* plants.

It is claimed:

1. A new and distinct *Anisodontea* plant named 'Oostanique' as illustrated and described.

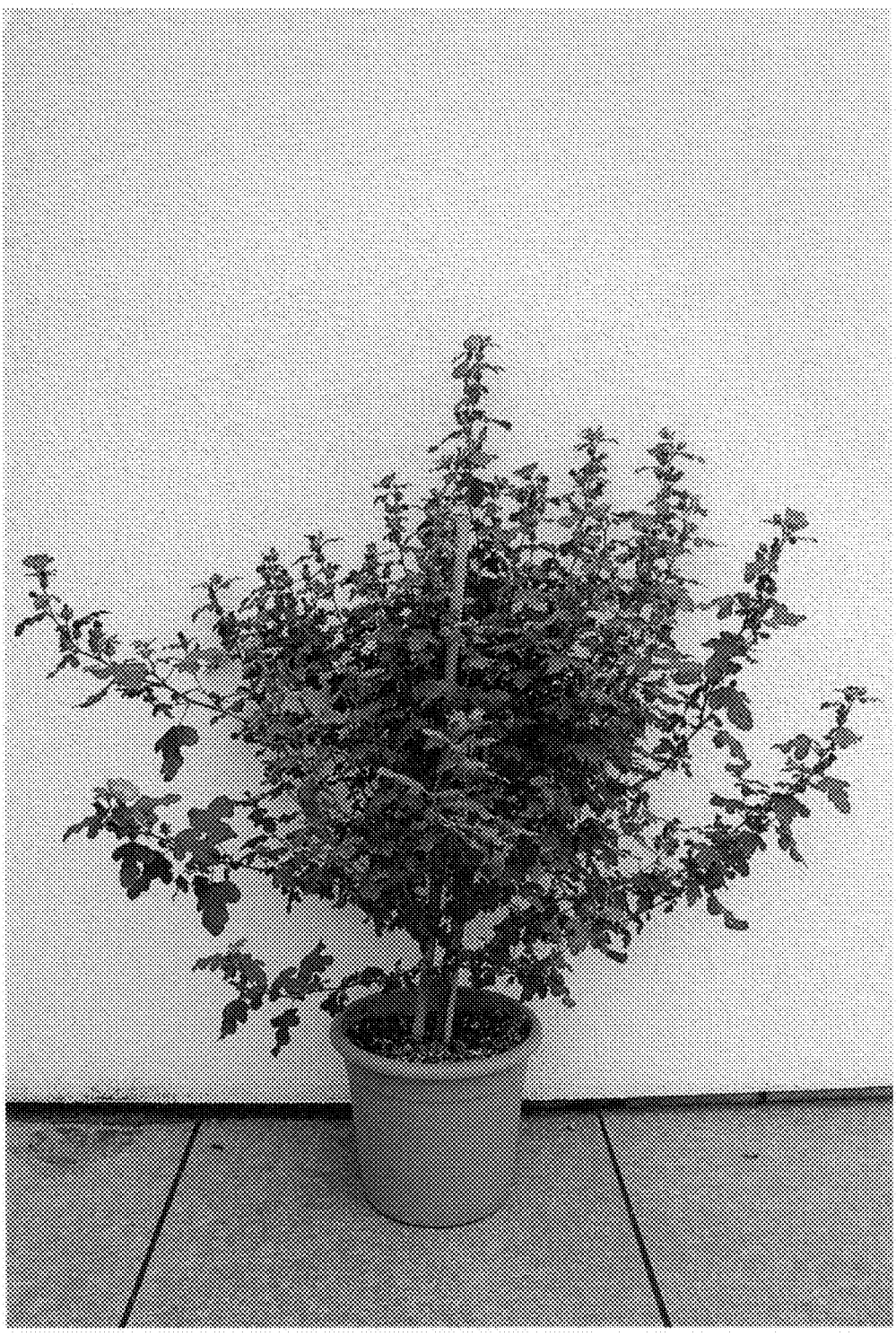

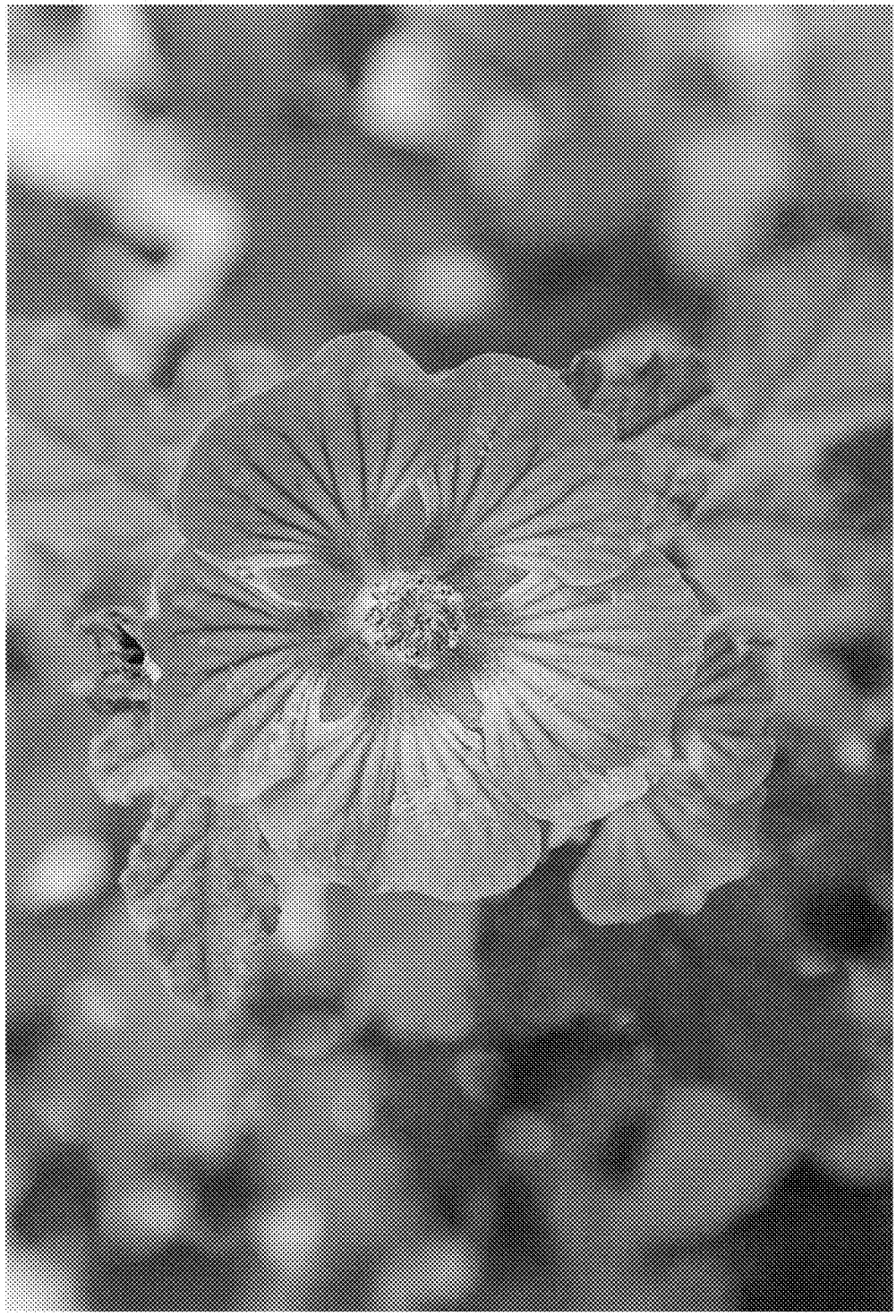

* * * * *